(12) United States Patent
Chang et al.

(10) Patent No.: US 9,017,952 B2
(45) Date of Patent: Apr. 28, 2015

(54) REAGENTS FOR PROBING ROCKS ACTIVATION

(71) Applicant: National Yang Ming University, Taipei (TW)

(72) Inventors: Zee-Fen Chang, Taipei (TW); Hsiao-Hui Lee, Taipei (TW)

(73) Assignee: National Yang Ming University, Taipei (TW)

( * ) Notice: Subject to any disclaimer, the term of this patent is extended or adjusted under 35 U.S.C. 154(b) by 36 days.

(21) Appl. No.: 13/686,717

(22) Filed: Nov. 27, 2012

(65) Prior Publication Data

US 2014/0030731 A1  Jan. 30, 2014

(30) Foreign Application Priority Data

Jul. 24, 2012 (TW) .............................. 101126665 A (51) Int. Cl.
| | |
|---|---|
| *G01N 33/53* | (2006.01) |
| *C07K 16/18* | (2006.01) |
| *C07K 16/40* | (2006.01) |
| *C07K 16/44* | (2006.01) |
| *G01N 33/50* | (2006.01) |

(52) U.S. Cl.
CPC ................ *C07K 16/40* (2013.01); *G01N 33/50* (2013.01); *C07K 16/18* (2013.01); *C07K 16/44* (2013.01); *C07K 2317/34* (2013.01)

(58) Field of Classification Search
USPC ................................ 436/501; 530/300, 387.1
See application file for complete search history.

(56) References Cited

U.S. PATENT DOCUMENTS

2007/0031940 A1*  2/2007  Van Rompaey et al. ..... 435/91.1

OTHER PUBLICATIONS

Chuang et al. ROCK II Ser1366 phosphorylation reflects the activation status. Biochem. J. vol. 443:145-151 (Apr. 2012).*
Chuang, et al., "ROCKII Serine 1366 phosphorylation reflects the activation status", Biochemical Journal Immediate Publication, Jan. 24, 2012, 26 pages, manuscript BJ20111839.

* cited by examiner

*Primary Examiner* — Elizabeth C Kemmerer
*Assistant Examiner* — Regina M Deberry
(74) *Attorney, Agent, or Firm* — Muncy, Geissler, Olds & Lowe, P.C.

(57) ABSTRACT

A set of agents is provided for probing/detecting the activation of Rho-associated protein kinase I and II individually encoding their amino acid sequence (SEQ ID NO:1 for ROCKI and SEQ ID NO:2 for ROCKII) in biological samples. The agents include one antibody to specifically recognize ROCKI Ser$^{1333}$ phosphorylation and one antibody to specifically recognize ROCKII Ser$^{1366}$ phosphorylation. The agents can be used for pathological analysis in cardiovascular diseases, cancer, neurological diseases or other diseases/disorders involving ROCKs and also for basic medical research. Moreover, the agents can be used for screening inhibitors against ROCKI and II.

10 Claims, 6 Drawing Sheets
(1 of 6 Drawing Sheet(s) Filed in Color)

REAGENTS FOR PROBING ROCKS ACTIVATION

CROSS-REFERENCE TO RELATED APPLICATIONS

This Non-provisional application claims priority under 35 U.S.C. §119(a) on Patent Application No(s). 101126665 filed in Taiwan, Republic of China Jul. 24, 2012, the entire contents of which are hereby incorporated by reference.

FIELD OF THE INVENTION

This invention relates to a detection reagent kit, in particularly, this invention relates to a reagent kit capable of probing the activations of ROCKI and ROCKII individually.

BACKGROUND OF THE INVENTION

Rho-associated protein kinases (ROCKs), the downstream effectors of Rho A, belong to the member of a serine/threonine protein kinase family. This molecule play key roles in many cellular processes, including the regulation of cell adhesion, migration, contractility, growth, apoptosis, centrosome duplication, and cytokinesis. ROCKs also play the key role in the occurrence of cardiovascular diseases, cancer and neurological diseases. Two ROCK isoforms, have been identified in mammals, ROCKI and ROCKII. They have the similar domain structure and composed of a kinase domain in the N-terminus, a RhoA-binding domain and a pleckstrin homology (PH) domain in the C-terminal region. The signaling pathways for regulating ROCK activity in cells includes: (1) the combination of RhoA and ROCK, (2) proteolytic cleavage of the C-terminal inhibitory domain in apoptotic cells, (3) the intracellular second messengers, such as arachidonic acid, or (4) the interaction with several proteins, such as stimulation by polo-like kinase-1 (Plk1) and nucleophosmin, and repression by GTP binding protein (Gem and Rad, for instance) and the ROCK inhibitor (Morgana).

Recently, the methods for detecting the ROCK activation including: (1) to indirectly determine ROCK phosphorylation by measuring the inhibitor-sensitive phosphorylation ROCK downstream subtracts (e.g. myosin light chain (MLC), myosin binding substrate (MBS), LIM kinase (LIMK), and α-adducin); or (2) to measure the catalytic activity of the purified ROCK kinase by in vitro kinase assay. However, the phosphorylation levels of ROCK downstream subtracts do not directly correspond to the respective activations of ROCKI or ROCKII in cells and tissues. And the ROCK kinase in vitro kinase assay requires high amount of purified ROCK protein that is unfavorable for detecting ROCK activity in cells and tissues. In addition, the loss of RhoA binding during sample preparation might result in the disadvantage of assay. There is no any method can directly and efficiently measure the respective activation of ROCKI and ROCKII. Therefore, these traditional methods are not sufficient to determine ROCKI and ROCKII activation in tissues to evaluate the relationship between the ROCKs activation and diseases such as cardiovascular diseases, cancer or neurological diseases.

It is therefore attempted by the applicant to deal with the above situation encountered in the prior art.

SUMMARY OF THE INVENTION

There are two ROCKs, ROCKI and ROCKII, in mammals. In our studies, We found that these two protein kinases are autophosphorylated upon activation. In order to find the method and tool for determining the activation of ROCKI and ROCKII directly and efficiently, we identified the phosphorylation sites in ROCKI and ROCKII individually and demonstrated that those phosphorylation indeed reflect to their activation. The present invention discloses a pair of specific antibodies those against the ROCKI and ROCKII phosphorylation individually and are used to evaluate the activation levels of ROCKI and ROCKII respectively. These antibodies can be further prepared as the detection kits, and thus the reagents can be applied for the detection of the ROCKI and ROCKII activation in the biological samples. The results will provide information for the reference to the pathological analysis of diseases for clinics and the clinically therapeutic administration. The detection reagent also can be applied in the relevant researches for the drug screening of ROCKI and ROCKII specific inhibitors.

Therefore, the present invention provides a kit for probing the activation of Rho-associated protein kinases (ROCKs) including ROCKI and ROCKII individually in the biological samples, wherein the kit includes an antibody-I for recognizing phosphorylated serine 1333 ($pSer^{1333}$) in the ROCKI peptide sequence (SEQ ID NO:1), an antibody-II for recognizing phosphorylated serine 1366 ($pSer^{1366}$) in the ROCKII peptide sequence (SEQ ID NO:2), a synthetic unphosphorylated peptide (oligopeptide-Ia) with the peptide sequence corresponding to antibody-I and a synthetic phosphorylated peptide (oligopeptide-Ib) with the same peptide sequence, and a synthetic unphosphorylated peptide (oligopeptide-IIa) with the peptide sequence corresponding to antibody-II and a synthetic phosphorylated peptide (oligopeptide-IIb) with the same peptide sequence.

Preferably, oligopeptide-Ia is a synthetic oligopeptide including the amino acid (a.a.) residues 1326 to 1336 of ROCKI (SEQ ID NO: 1), and has an amino acid sequence of N'-RASPRTLSTRS-C' (SEQ ID NO:3). Oligopeptide-Ib is a synthetic oligopeptide which has the same sequence as oligopeptide-Ia but the second serine is phosphorylated; therefore, the oligopeptide-Ib has an amino acid sequence of N'-RASPRTLpSTRS-C' (SEQ ID NO:4). Oligopeptide-IIa is a synthetic oligopeptide including the amino acid residues 1356 to 1368 of ROCKII (SEQ ID NO: 2), and has the same sequence as oligopeptide-Ia but the third serine is phosphorylated; therefore, theoligopeptide-IIb has an amino acid sequence of N'-DPFARSSPRTpSMK-C' (SEQ ID NO:6).

Oligopeptide-Ib acts as the antigen to immunize animals, so that the phospho-specific antibody-I is generated and purified to recognize $Ser^{1333}$ phosphorylation of ROCKI that indicates the activation of ROCKI kinase activity. Oligopeptide-Iib acts as the antigen to immunize animals, so that the phospho-specific antibody-II is generated and purified to recognize $Ser^{1366}$ phosphorylation of ROCKII that indicates the activation of ROCKII kinase activity. Using antibody-I and antibody-II to probe the biological samples, protein extracts from cells or tissue could be analyzed by Western blotting; the fixed cells or tissue sections could be probe by immunohistochemical staining. At the same time, the phosphorylated peptides (oligopeptide-Ib and oligopeptide-IIb) and the unphosphorylated peptides (oligopeptide-Ia and oligopeptide-IIa) are used to proceed the antibody neutralization to identify those signals are indeed reflect to the phosphorylation of ROCKI and ROCKII individually, so as to further analyze the respective phosphorylation levels of ROCKI and ROCKII in the biological samples. The reaction performed by the addition of the phosphorylated peptide and the antibody acts as the negative control. If the signal of the antibody reaction is positive in the present of unphosphorylated peptide, it refers to that the molecules (ROCKI and ROCKII) are activated, and the signal intensities are proportional to the levels of kinase activities. Otherwise, if the signal is negative or the intensity is equal with the signal in negative control reaction, the molecules (ROCKI and ROCKII) are not activated.

The above biological samples are originated from a subject being subjected to or suspected to be subjected to a disease, and the disease may be but is not limited to liver tumor, breast cancer, leukemia, melanoma, prostate cancer, lung cancer, cardiovascular diseases and/or neurological diseases. Additionally, the subject is a human or other mammals, and the biological samples are cellular or tissue samples.

The above reagents includes an antibody-I for recognizing Ser$^{1333}$ phosphorylation of ROCKI, an antibody-II for recognizing Ser$^{1366}$ phosphorylation of ROCKII, a synthetic oligopeptide-Ia including a peptide sequence of N'-RASPRTL-STRS-C' (SEQ ID NO:3), a synthetic oligopeptide-Ib including a peptide sequence of V-RASPRTLpSTRS-C (SEQ ID NO:4), a synthetic oligopeptide-IIa including a peptide sequence of N'-DPFARSSPRTSMK-C' (SEQ ID NO:5), and a synthetic oligopeptide-IIb including a peptide sequence of N'-DPFARSSPRTpSMK-C' (SEQ ID NO:6). Each of antibody-I and -II and oligopeptide-Ia, -Ib, -IIa and -IIb in the reagent has a lowest effective amount to represent their function and effect. For Western blotting, the amount of antibody is used about 0.5 µg/ml to 2 µg/ml, and the amount of oligopeptide is used about 0.1 µg/ml to 1 µg/ml. For immunohistochemical staining, the amount of antibody is used about 2 µg/ml to 5 µg/ml, and oligopeptide is used about 0.4 µg/ml to 2.5 µg/ml.

The present invention further provides two antibodies for recognizing ROCKI or ROCKII, respectively. ROCKI is encoded with a peptide-I sequence (SEQ ID NO:1), wherein antibody-I is capable of recognizing Ser$^{1333}$ phosphorylation of peptide-I sequence. ROCKII is encoded with a peptide-II sequence (SEQ ID NO:2), wherein antibody-II is capable of recognizing Ser$^{1366}$ phosphorylation of peptide-II sequence.

Preferably, the antibody includes two antigen binding domains, each of which is composed of a light chain variable ($V_L$) domain and a heavy chain variable ($V_H$) domain. The antigen binding domains of antibody-I can recognize Ser$^{1333}$ phosphorylation of ROCKI, and those of antibody-II can recognize Ser$^{1366}$ phosphorylation of ROCKII.

The present invention further provides a method for probing ROCKI activation or ROCKII activation in a biological sample. ROCKI has a peptide-I sequence (SEQ ID NO:1) with Ser$^{1333}$ residue, and ROCKII has a peptide-II sequence (SEQ ID NO:2) with Ser$^{1366}$ residue. The method includes: (I) providing an antibody-I capable of recognizing Ser$^{1333}$ phosphorylation of ROCKI and an oligopeptide-Ia encoding a sequence of N'-RASPRTLSTRS-C' (SEQ ID NO:3); mixing the antibody-I and the oligopeptide-Ia as a first mixture; and adding the first mixture to the biological sample, wherein ROCKI is activated in the biological sample and the signal intensity indicates to the kinase level of ROCKI when a positive signal is generated; and ROCKI is not activated therein when the negative signal is generated; and (2) providing an antibody-II capable of recognizing Ser$^{1366}$ phosphorylation of ROCKII and an oligopeptide-IIa encoding a sequence of N'-DPFARSSPRTSMK-C' (SEQ ID NO:5); mixing the antibody-II and the oligopeptide-IIa as a second mixture; and adding the second mixture to the biological sample, wherein ROCKII is activated in the biological sample and the signal intensity indicates to the kinase level of ROCKII when a positive signal is generated; and ROCKII is not activated therein when a negative signal is generated.

The method (1) further includes: (3) providing an oligopeptide-Ib encoding a sequence of N'-RASPRTLpSTRS-C' (SEQ ID NO:4); mixing the antibody-I and the oligopeptide-Ib as a third mixture; and adding the third mixture to the biological sample. Since the second serine numbered from the N-terminus of oligopeptide-Ib is phosphorylated, oligopeptide-Ib may be conjugated with the antibody to neutralize the antibody, such that antibody-I cannot recognize the activated ROCKI in the biological sample and thus the result is determined as the negative signal. The method (2) further includes: (4) providing an oligopeptide-IIb encoding a sequence of N'-DPFARSSPRTpSMK-C' (SEQ ID NO:6); mixing the antibody-II and the oligopeptide-IIb as a fourth mixture; and adding the fourth mixture to the biological sample. Since the third serine numbered from the N-terminus of oligopeptide-IIb is phosphorylated, oligopeptide-IIb may be conjugated with the antibody to neutralize the antibody, such that antibody-II cannot recognize the activated ROCKII in the biological sample and thus the result is determined as the negative signal. The results of the methods (3) and (4) are the negative control for the detection method of the present invention.

The present invention further provides a method for detecting the catalytic activity of ROCKI and ROCKII. ROCKI has a peptide-I sequence (SEQ ID NO:1) with Ser$^{1333}$ residue, and ROCKII has a peptide-II sequence (SEQ ID NO:2) with Ser$^{1366}$ residue. The method can be used to screen the specific ROCKI and ROCKII inhibitors by determining the inhibitory effect of the drugs on the catalytic activity of ROCKI and ROCKII, respectively.

The detailed technologies and the preferred embodiments of the present invention will be described in the following contents for one skilled in the art to appreciate the features of the present invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

For clarity of disclosure, and not by way of limitation, the detailed description of the invention is divided into the subsections that follow.

Experimental Methods:

The various gene constructs were formed by using QuikChange® Site-Directed Mutagenesis Kit (Stratagene) to individually introduce the specific mutations to the wild-type (WT) pEF-myc-ROCKII (6-1388) (from K. Kaibuchi; Nara Institute of Science and Technology, Ikoma, Japan) or pCMV2-flag-ROCKI plasmid.

I. Immunoprecipitation and In Vitro Kinase Reaction:

myc-ROCKII-expressing cells were harvested in an immunoprecipitation (IP) buffer (1% NP-40, 5% glycerol, 50 mM Tris/HCl, pH 7.4, 150 mM NaCl, 1 mM PMSF (phenylmethylsulfonyl fluoride), and protease inhibitor cocktail). The lysates after pre-clearance were incubated with anti-myc antibody at 4° C. for 60 minutes, and then precipitated with protein A-agarose beads for 30 minutes. The immunoprecipitates were preincubated with or without 100 µM of Y27632 (ROCK inhibitor), which was followed by incubation with a IX kinase buffer (50 mM Tris/HCl, pH 7.4, 10 mM MgCl$_2$, 1 mM EGTA (ethylene glycol tetraacetic acid), 0.5 mM DTT (dithiothreitol), 5 mM NaF, and 0.1 mM Na$_3$VO$_4$, 20 µM ATP) containing 5 µCi of [γ-$^{32}$p]ATP at 30° C. for 20 minutes. The immunoprecipitates (controls) from non-transfected cells were used backgrounds. The protein level of myc-ROCKII was detected by Western blotting with anti-myc antibody known by the skilled person in the art. The protein level of flag-ROCKI was probed using the similar immunoprecipitation and Western blotting with anti-flag antibody II. In-Gel Digestion and LC-MS/MS:

The protein band corresponding to myc-ROCKII was excised from the gel for protease digestion as described by Tsay et al. (Anal. Biochem. 2000. 287: 55-64). In brief, proteins were digested with Lys-C, Arg-C and Asp-N (the multiple enzymes used to increase sequence coverage), and the peptides were extracted with 0.1% formic acid. Electrospray ionization-ion trap tandem mass spectrometry was performed using a Thermo Finnigan LTQ Orbitrap tandem mass spectrometer interfaced with an Agilent 1100D HPLC system. The spectra for elute was acquired as successive sets of scan modes described by Tsay et al. (Anal. Biochem. 2000. 287: 55-64), which included (1) identification of phosphopeptides on selected ion tracings based on their elution behavior, (2) mapping phosphorylated amino acids within the sequence by collision-induced dissociation (CID) experiments, and (3) using the selected ion tracing method to quantitatively determine the phosphorylation states of myc-ROCKII proteins.

III. Phospho-Specific Antibody Generation:

The specific polyclonal anti-pSer$^{1333}$ ROCKI antibody was raised using the phosphopeptide-Ib containing pSer$^{1333}$ of ROCKI conjugated with keyhole limpet haemocyanin (KLH) as an antigen to immune rabbits. The anti-sera were collected and sequentially affinity-purified by the phosphopeptide- and the non-phosphopeptide-conjugated columns to remove the non-anti-phosphorylation antibody. The anti-sera were desalted and concentrated to obtain the specific polyclonal anti-pSer$^{1333}$ ROCKI antibody (antibody-I). The specific polyclonal anti-Ser$^{1366}$ ROCKII antibody was raised using the phosphopeptide-IIb containing pSer$^{1366}$ of ROCKII conjugated with KLH as an antigen to immunize rabbits. The anti-sera were collected and sequentially affinity-purified by the phosphopeptide- and the non-phosphopeptide-conjugated columns to remove the non-anti-phosphorylation antibody. The anti-sera were desalted and concentrated to obtain the specific polyclonal anti-pSer$^{1366}$ ROOKIE antibody (antibody-II).

IV. Immunohistochemical (IHC) Staining:

The tumor part and the non-tumor part of the breast tissue blocks were embedded in Tissue-Tek OCT™ compound, snap-frozen, and sectioned into 5 µm cryosections. The sections were fixed with 4% (w/v) paraformaldehyde for 15 minutes and placed in boiling citrate buffer for 10 minutes. Endogenous peroxidase activity was quenched by 3% hydrogenous peroxidase for 10 minutes and this was followed by incubation with 5.5% (v/v) normal goat serum in Tris-buffer saline containing 0.1% of Triton X-100 (TBST) for blocking. Sections were subsequently incubated with primary antibody against pSer$^{1366}$ ROCKII (1:200 dilution; 5 µg/ml) in the present or absence of the phosphopeptide or non-phosphopeptide (0.5 µg/ml). After extend washing, the sections were incubated with horseradish peroxidease (HRP)-conjugated anti-rabbit antibody and then developed by 3,3-di-aminobenzidine (DAB) solution for 3 minutes. Slides were counterstained with hematoxylin, which was followed by dehydration then mounting.

Experimental Results:

The myc-ROCKII protein overexpressed in HEK-293T cells was immunoprecipitated and subjected to an in vitro kinase reaction containing [γ-$^{32}$P]ATP in the presence or absence of the ROCK inhibitor Y27632. Radioactively labeled ROCKII was detected and Y27632 treatment abolished the phosphorylation signal, indicating that the autophosphorylation occurred on the ROCKII protein of the present invention. To identify the phosphorylation sites, the immunoprecipitated ROCKII was incubated with nonradioactive ATP in a kinase reaction, followed by SDS-PAGE (sodium dodecyl sulfate polyacrylamide gel electrophoresis) separation. The protein band corresponding to myc-ROCKII was digested with Lys-C, Arg-C or Asp-N to increase the total sequence coverage (78.3%) for LC-MS/MS analysis. Three Y27632-sensitive phosphopeptides were found. Judging from the increased mass of 79.96 Da in the spectra, each peptide contains a monophosphorylation at the Thr$^{1365}$/Ser$^{1366}$, Ser$^{1374}$ or Ser$^{1379}$ sites (data not shown).

Figure 1A:
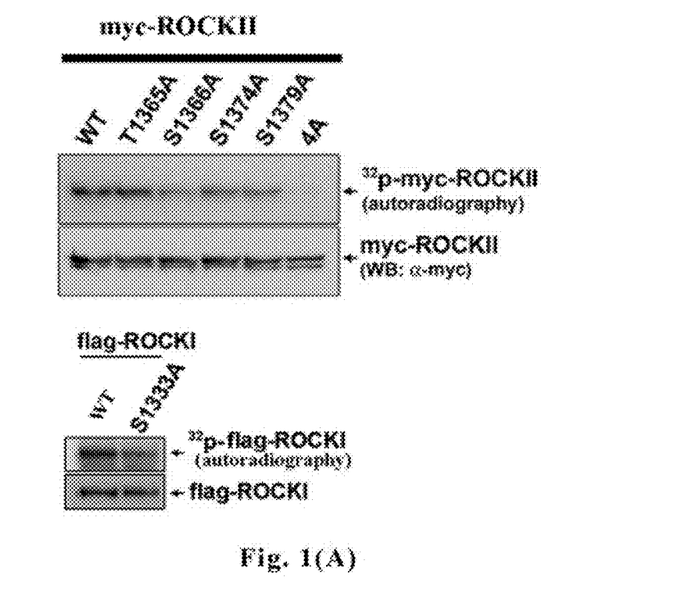
FIG. 1(A) illustrates the isotope-labeled autoradiography showing the in vitro kinase reaction after the wild-type (WT) myc-ROCKII and its mutant and the WT flag-ROCKI and its mutant are expressed in HEK-293T cells.
Figure 1B:
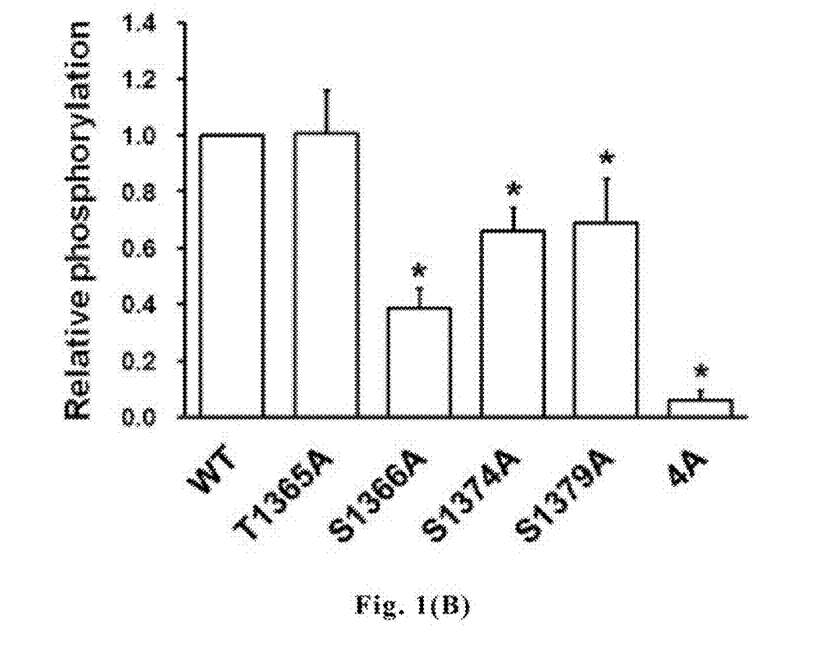
FIG. 1(B) illustrates the bar chart of relative phosphorylation of myc-ROCKII WT and its mutant.

Subsequently, the contribution of Thr$^{1365}$, Ser$^{1366}$, Ser$^{1374}$ and Ser$^{1379}$ residues in the phosphorylation of myc-ROCKII carrying an alanine (Ala) mutation in these sites was tested. Please refer to FIG. 1, FIG. 1A showed the autoradiography on $^{32}$P-myc-ROCKII phosphorylation and the Western blotting spectrum against myc-ROCKII of the WT and the mutants (T1365A, S1366A, S1374A, S1379A, and 4A with mutations at these four sites), and the autoradiography on $^{32}$P-flag-ROCKI and the Western blotting spectrum against flag-ROCKI of the flag-ROCKI WT and the mutant (S1333A); and FIG. 1B showed the bar chart of relative phosphorylation of myc-ROCKII WT and the mutant. The mutant of S1366A (i.e. serine 1366 was mutated as alanine) gave a clear reduction in the intensity of [γ-$^{32}$P]ATP labeling in contrast to no effect in the T1365A mutation, excluding T1365, in phosphorylation. Mutation at either the Ser$^{1374}$ or Ser$^{1379}$ sites (S1374A or Ser1379A respectively) reduced the radioactive labeling intensity, but not as much as the S1366A mutation. Four Ala substitutions (i.e. the mutant "4A") almost completely abolished the radioactive labeling signal of myc-ROCKII. Accordingly, ROCKII is autophosphorylated at the Ser$^{1366}$, Ser$^{1374}$ and S$^{1379}$ residues with the highest distribution at the Ser1366 site.

Figure 2A:
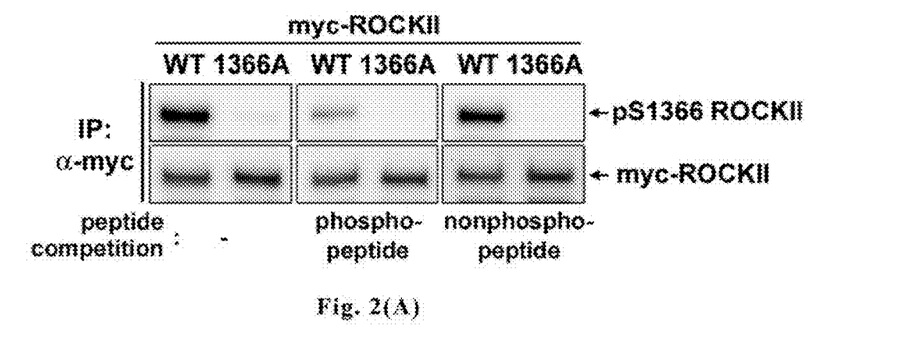
FIG. 2(A) illustrates the Western blotting pattern showing anti-pSer$^{1366}$ ROCKII antibody-II against the phosphorylated ROCKII. myc-ROCKII protein is obtained with extraction after the WT or S1366A mutant myc-ROCKII expression constructs are respectively transfected into HEK-293T cells and immunoprecipitated using anti-myc antibody, and Ser$^{1366}$ phosphorylation of myc-ROCKII is probed with antibody-II (1 µg/ml) with or without the competition of phosphorylated peptide-IIa (0.2 µg/ml).
Figure 2B:
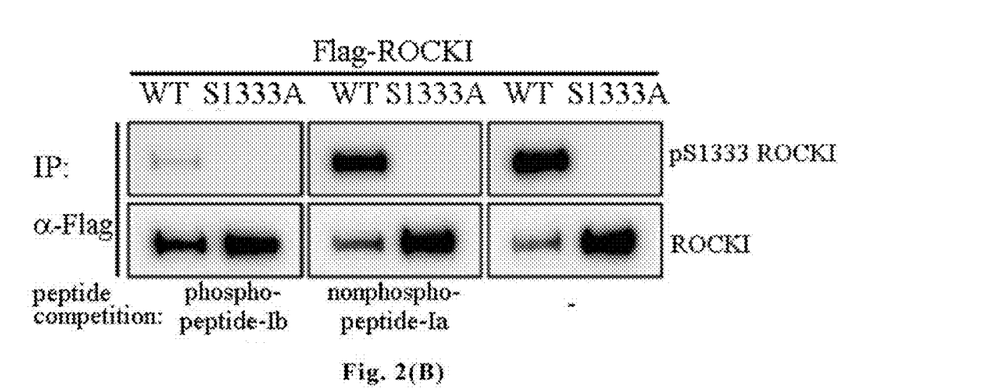
FIG. 2(B) illustrates the Western blotting pattern showing anti-pSer$^{1333}$ ROCKI antibody-I against the phosphorylated ROCKI. flag-ROCKI protein is obtained with extraction after the WT or S1333A mutant flag-ROCKI expression constructs are respectively transfected to FMK-293T cells and immunoprecipitated using anti-flag antibody, and Ser$^{1333}$ phosphorylation of flag-ROCKI is probed with antibody-I (1 µg/ml) with or without the competition of phosphorylated peptide-Ia (0.2 µg/ml).

To determine whether phosphorylation at the Ser$^{1366}$ site is a mark of active ROCKII in biological samples, we generated anti-pSer$^{1366}$ ROCKII antibody, which was capable of detecting the in vitro autophosphorylation of immunoprecipitated WT but not S1366A myc-ROCKII by Western blotting, and the aforementioned autophosphorylated signal was neutralized by phosphorylated peptide-Ib but not unphosphorylated peptide-IIa (FIG. 2(A)), We also generated anti-pSer$^{1333}$ ROCKI antibody, which was capable of detecting the in vitro autophosphorylation of immunoprecipitated WT flag-ROCKI but not S1333A flag-ROCKI by Western blotting, and the aforementioned autophosphorylated signal was neutralized by phosphorylated peptide-Ib but not unphosphorylated peptide-Ia (FIG. 2(B)).

Figure 3:
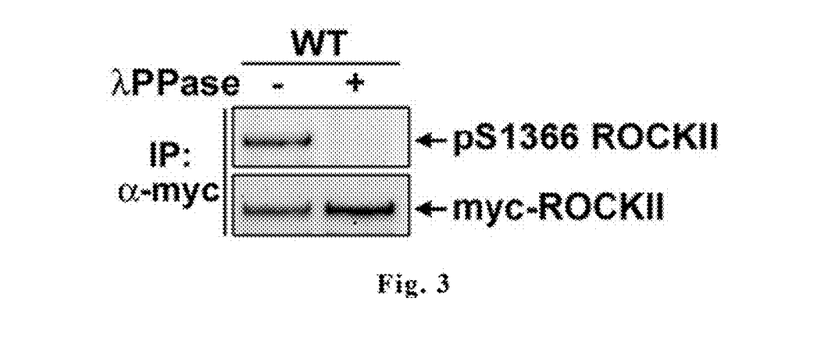
FIG. 3 illustrates the Western blotting pattern showing the signal of immunoprecipitated WT myc-ROCKII with or without λ protein phosphatase (λPPase) at 30° C. for 20 minutes treatment probed with antibody-II
Figure 4:
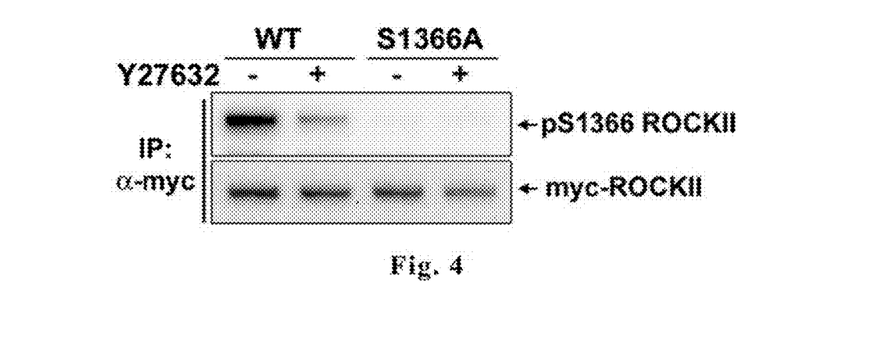
FIG. 4 illustrates the Western blotting pattern showing the signal of immunoprecipitated WT or S1366A myc-ROCKII expressed in HEK293T cells which were treated with or without Y27632 (20 µM) for 2 hours before harvested for IP and probing with antibody-II.

Treatment of myc-ROCKII immunoprecipitates with λ protein phosphatase (λPPase) abolished the antibody detection signal (FIG. 3), indicating its specificity in detecting phosphorylated ROCKII. Furthermore, the signal level of Ser$^{1366}$ phosphorylated myc-ROCKII was markedly decreased in cells treated with Y27632 (ROCK inhibitor) (FIG. 4). Accordingly, ROCKII Ser$^{1366}$ phosphorylation can be the indication for ROCKII activation.

Figure 5A:
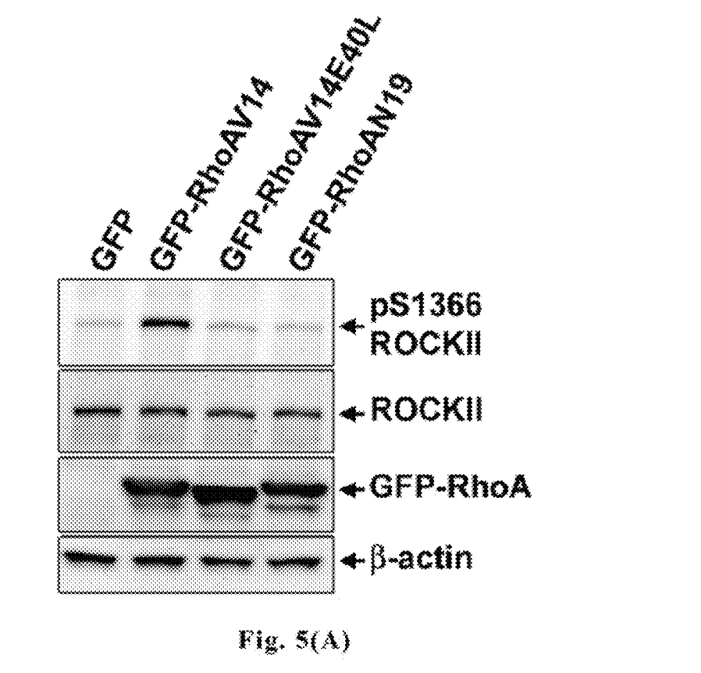
FIGS. 5(A) and 5(B) respectively illustrate the Western blotting patterns showing (A) antibody-I and (B) antibody-II against the protein extract of the HEK-293T cells expressed GFP, GFP-RhoAV14, GFP-RhoAV14E40L, or GFP-RhoAV19.
Figure 5B:
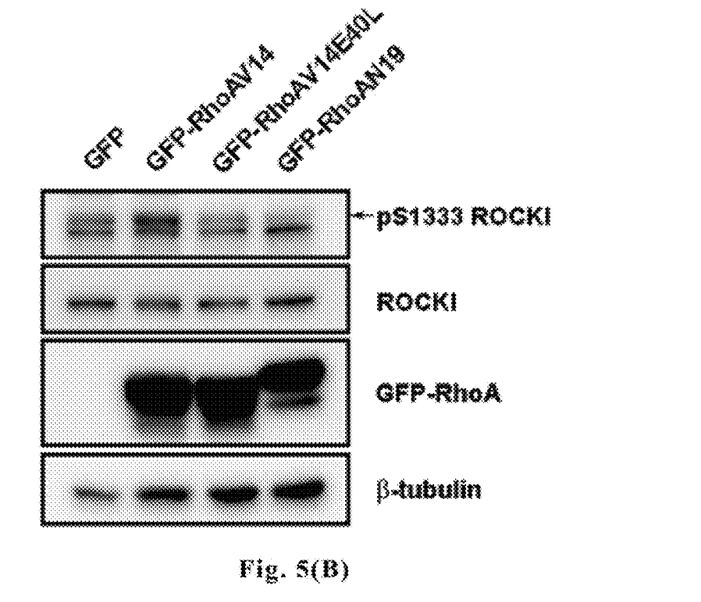

Next, we tested whether Ser$^{1366}$ phosphorylation on endogenous ROCKII can be detected in response to RhoA activation in cells. Please refer to FIG. 5, a green fluorescence protein (GFP)-labeled RhoA, a constitutively active GFP-RhoAV14, a constitutively active mutant of RhoA defective in its interaction with ROCK (Sahai et al., EMBO J. 1998. 17: 1350-1361.), a dominant negative form of GFP-RhoAN19 and a GFP expression vector (control) respectively are transfected into and expressed in HEK-293T cells, and cellular protein extracts were proceeded via electrophoresis and Western blotting. The detection result of antibody-II revealed that the level of ROCK Ser$^{1366}$ phosphorylation in the GFP-RhoAV14 expression cells was enhanced but neither GFP-RhoAV14E40L nor GFP-RhoAN19 transfection shows no the enhancement of RCOKII Ser$^{1366}$ phosphorylation (FIG. 5(A)). The detection result of antibody-I revealed that the changes on the level of ROCKI Ser$^{1333}$ phosphorylation also indeed enhanced due to RhoA activation (FIG. 5(B)). It is shown from these results that the level of endogenous ROCKI and ROCKII activation in cells indeed can be detected using antibody-I and antibody-II respectively.

Figure 6A:
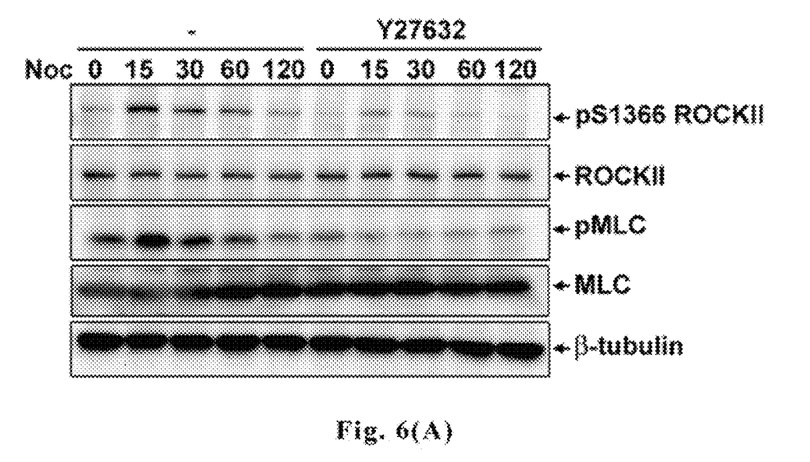
FIGS. 6(A) and 6(B) respectively illustrate the Western blotting patterns showing (A) antibody-I and (B) antibody-II against the protein extract from normal mouse embryonic fibroblasts (MEFs) stimulated with nocodazole(10 µM) in present or absent of Y27632 (10 µM).
Figure 6B:
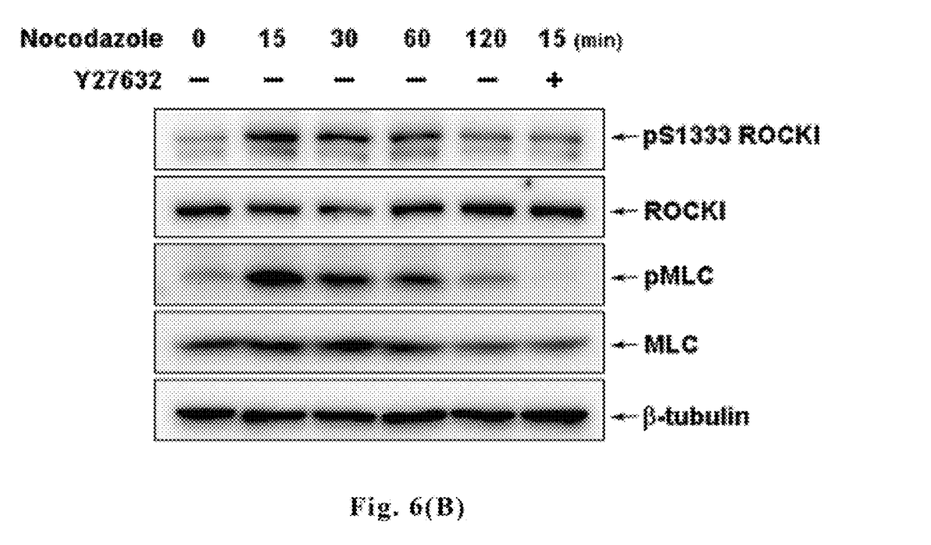

In addition to the above human cell experiments, the level of Ser$^{1366}$ phosphorylation of ROCKII in animal cells is also researched in the present invention. Mouse embryonic fibroblasts (MEFs) were serum-starved for 24 hours and treated with mitotic inhibitor (nocodazole, 10 μM, a reagent to result in RhoA. activation) with or without Y27632 (10 μM), and it is found that the signal of ROCKII Ser$^{1366}$ phosphorylation will be enhanced and the downstream phosphor-MLC signal regulated by ROCKII also is markedly increased (FIG. 6(A)). The phenomenon of the aforementioned enhanced phosphorylation signal will be disappeared after the administration of ROCK inhibitor Y27632 (10 μM). Similarly, ROCKI activation also can be detected (FIG. 6(B)). Accordingly, the level of ROCKII Ser$^{1366}$ phosphorylation can reflect RhoA-regulated ROCKII activation, and that of ROCKI Ser$^{1333}$ phosphorylation can reflect RhoA-regulated ROCKI activation.

Figure 7:
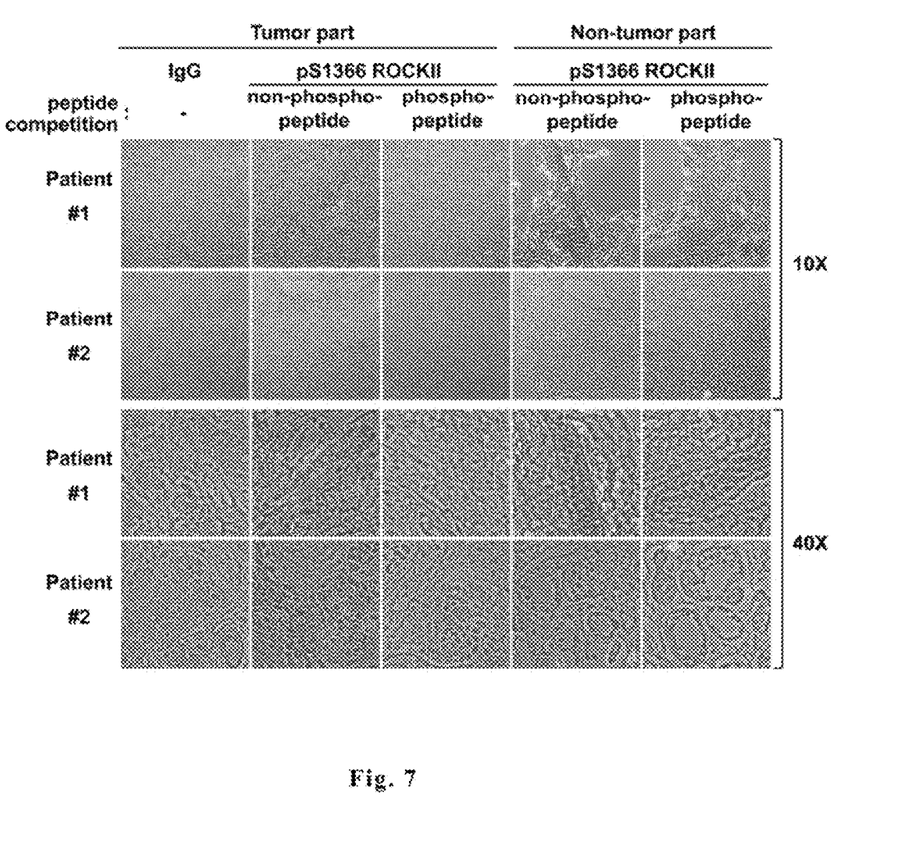
FIG. 7 illustrates the immunohistochemistry images showing RCOKII Ser$^{1366}$ phosphorylation in human breast tumor tissues. The tumor part and non-tumor part breast tissues of from two breast cancer patients are sectioned, and probed with anti-pSer$^{1366}$ ROCKII antibody in the presence of phosphorylated peptide-Ib and unphosphorylated peptide-IIa. The normal rabbit IgG is the control for negative reaction, and #1 is negative for lymph node and #2 is positive for lymph node.

Next, whether ROCKII Ser$^{1366}$ phosphorylation can be detected is determined by anti-pSer$^{1366}$ ROCKII antibody-II. Please refer to IHC staining patterns of FIG. 7, ROCKII Ser$^{1366}$ phosphorylation signal (brown color) is probed using anti-pSer$^{1366}$ ROCKII antibody-II in the breast tumor tissue sample from human patients with breast cancer. The phosphorylation signal can be blocked by the competition of phosphopeptide-IIb (phosphorylation at Ser$^{1366}$ residue of N'-DP-FARSSPRTpSMK-C' (SEQ ID NO:6)), indicating the specificity between anti-pSer$^{1366}$ ROCKII antibody and ROCKII Ser$^{1366}$ phosphorylation. Accordingly, anti-pSer$^{1366}$ ROCKII antibody can act as the tool for evaluating ROCKII activation of the sample.

Although the present invention has been described in terms of specific exemplary embodiments and examples, it will be appreciated that the embodiments disclosed herein are for illustrative purposes only and various modifications and alterations might be made by those skilled in the art without departing from the spirit and scope of the invention as set forth in the following claims.

What is claimed is:

1. A reagent for probing the activation of a Rho-associated protein kinase II (ROCKII) in a biological sample from a mammal, the ROCKII comprising a peptide-II sequence, wherein the reagent comprises an antibody-II that specifically binds to a phosphorylated serine amino acid at position 1366 in SEQ ID NO:2 but does not bind when serine amino acid at position 1366 in SEQ ID NO:2 is not phosphorylated.

2. The reagent according to claim 1, wherein the peptide-II sequence has an oligopeptide sequence of DPFARSSPRTSMK (SEQ ID NO:5) from an N-terminal to a C-terminal.

3. The reagent according to claim 2, wherein a third serine numbered from the N-terminal of the oligopeptide sequence is phosphorylated.

4. The reagent according to claim 1, wherein the biological sample is originated from a subject being subjected to or suspected to be subjected to a disease, and the disease is selected from a group consisting of liver tumor, breast cancer, leukemia, melanoma, prostate cancer, lung cancer, cardiovascular diseases, neurological diseases and a combination thereof.

5. The reagent according to claim 4, wherein the subject is a human or a mammal excluding the human.

6. The reagent according to claim 1, wherein the reagent further comprises an oligopeptide-IIa with a sequence of N'-DPFARSSPRTSMK-C' (SEQ. NO: 5) and an oligopeptide-IIb with a sequence of N'-DPFARSSPRTpSMK-C' (SEQ. ID NO:6).

7. The reagent according to claim 1, wherein the peptide-II sequence is SEQ ID NO:2.

8. An antibody-II for recognizing a Rho-associated protein kinase II (ROCKII) having a peptide-II sequence, wherein said antibody-II specifically binds to a phosphorylated serine amino acid at position 1366 in SEQ ID NO:2 but does not bind when serine amino acid at position 1366 in SEQ ID NO:2 is not phosphorylated.

9. A method for probing the activation of a Rho-associated protein kinase II (ROCKII) in a biological sample, the ROCKII comprising a peptide-II sequence with a serine 1366 phosphorylation, the method comprising:
(a) providing an antibody-II that specifically binds to a phosphorylated serine amino acid at position 1366 in SEQ. ID NO:2 but does not bind when serine amino acid at position 1366 in SEQ ID NO:2 is not phosphorylated and an oligopeptide-IIa comprising a sequence of N'-DPFARSSPRTSMK-C'(SEQ ID NO:5);

(b) mixing the antibody-II and the oligopeptide-IIa as a second mixture; and
(c) adding the second mixture to the biological sample from a mammal, wherein the ROCKII is activated in the biological sample when a positive signal is generated, and the ROCKII is not activated therein when a negative signal is generated.

10. The method according to claim 9, wherein the step (a) further comprises:
   (a1) providing an oligopeptide-lib comprising a sequence of N'-DPFARSSPRTpSMK-C'(SEQ. ID NO:6);
   (a2) mixing the antibody-II and the oligopeptide-IIb as a fourth mixture; and
   (a3) adding the fourth mixture to the biological sample to determine as the negative signal as a negative control of the method.

\* \* \* \* \*

SEQUENCE LISTING

```
<160> NUMBER OF SEQ ID NOS: 6

<210> SEQ ID NO 1
<211> LENGTH: 1354
<212> TYPE: PRT
<213> ORGANISM: Homo sapiens
<220> FEATURE:
<221> NAME/KEY: misc_feature
<223> OTHER INFORMATION: Rho-associated protein kinase 1 (ROCKI)

<400> SEQUENCE: 1

Met Ser Thr Gly Asp Ser Phe Glu Thr Arg Phe Glu Lys Met Asp Asn
```

-continued

```
1               5                    10                   15
Leu Leu Arg Asp Pro Lys Ser Glu Val Asn Ser Asp Cys Leu Leu Asp
                20                   25                  30

Gly Leu Asp Ala Leu Val Tyr Asp Leu Asp Phe Pro Ala Leu Arg Lys
                35                   40                  45

Asn Lys Asn Ile Asp Asn Phe Leu Ser Arg Tyr Lys Asp Thr Ile Asn
 50                       55                   60

Lys Ile Arg Asp Leu Arg Met Lys Ala Glu Asp Tyr Glu Val Val Lys
 65                       70                   75                  80

Val Ile Gly Arg Gly Ala Phe Gly Glu Val Gln Leu Val Arg His Lys
                85                   90                  95

Ser Thr Arg Lys Val Tyr Ala Met Lys Leu Leu Ser Lys Phe Glu Met
                100                  105                 110

Ile Lys Arg Ser Asp Ser Ala Phe Phe Trp Glu Glu Arg Asp Ile Met
                115                  120                 125

Ala Phe Ala Asn Ser Pro Trp Val Val Gln Leu Phe Tyr Ala Phe Gln
                130                  135                 140

Asp Asp Arg Tyr Leu Tyr Met Val Met Glu Tyr Met Pro Gly Gly Asp
145                      150                  155                 160

Leu Val Asn Leu Met Ser Asn Tyr Asp Val Pro Glu Lys Trp Ala Arg
                165                  170                 175

Phe Tyr Thr Ala Glu Val Val Leu Ala Leu Asp Ala Ile His Ser Met
                180                  185                 190

Gly Phe Ile His Arg Asp Val Lys Pro Asp Asn Met Leu Leu Asp Lys
                195                  200                 205

Ser Gly His Leu Lys Leu Ala Asp Phe Gly Thr Cys Met Lys Met Asn
210                      215                  220

Lys Glu Gly Met Val Arg Cys Asp Thr Ala Val Gly Thr Pro Asp Tyr
225                      230                  235                 240

Ile Ser Pro Glu Val Leu Lys Ser Gln Gly Gly Asp Gly Tyr Tyr Gly
                245                  250                 255

Arg Glu Cys Asp Trp Trp Ser Val Gly Val Phe Leu Tyr Glu Met Leu
                260                  265                 270

Val Gly Asp Thr Pro Phe Tyr Ala Asp Ser Leu Val Gly Thr Tyr Ser
                275                  280                 285

Lys Ile Met Asn His Lys Asn Ser Leu Thr Phe Pro Asp Asp Asn Asp
290                      295                  300

Ile Ser Lys Glu Ala Lys Asn Leu Ile Cys Ala Phe Leu Thr Asp Arg
305                      310                  315                 320

Glu Val Arg Leu Gly Arg Asn Gly Val Glu Glu Ile Lys Arg His Leu
                325                  330                 335

Phe Phe Lys Asn Asp Gln Trp Ala Trp Glu Thr Leu Arg Asp Thr Val
                340                  345                 350

Ala Pro Val Val Pro Asp Leu Ser Ser Asp Ile Asp Thr Ser Asn Phe
                355                  360                 365

Asp Asp Leu Glu Glu Asp Lys Gly Glu Glu Glu Thr Phe Pro Ile Pro
                370                  375                 380

Lys Ala Phe Val Gly Asn Gln Leu Pro Phe Val Gly Phe Thr Tyr Tyr
385                      390                  395                 400

Ser Asn Arg Arg Tyr Leu Ser Ser Ala Asn Pro Asn Asp Asn Arg Thr
                405                  410                 415

Ser Ser Asn Ala Asp Lys Ser Leu Gln Glu Ser Leu Gln Lys Thr Ile
                420                  425                 430
```

```
        Tyr Lys Leu Glu Glu Gln Leu His Asn Glu Met Gln Leu Lys Asp Glu
                    435                 440                 445

Met Glu Gln Lys Cys Arg Thr Ser Asn Ile Lys Leu Asp Lys Ile Met
            450                 455                 460

Lys Glu Leu Asp Glu Gly Asn Gln Arg Arg Asn Leu Glu Ser Thr
        465                 470                 475                 480

Val Ser Gln Ile Glu Lys Glu Lys Met Leu Leu Gln His Arg Ile Asn
                        485                 490                 495

Glu Tyr Gln Arg Lys Ala Glu Gln Glu Asn Glu Lys Arg Arg Asn Val
                    500                 505                 510

Glu Asn Glu Val Ser Thr Leu Lys Asp Gln Leu Glu Asp Leu Lys Lys
                        515                 520                 525

Val Ser Gln Asn Ser Gln Leu Ala Asn Glu Lys Leu Ser Gln Leu Gln
                    530                 535                 540

Lys Gln Leu Glu Glu Ala Asn Asp Leu Leu Arg Thr Glu Ser Asp Thr
        545                 550                 555                 560

Ala Val Arg Leu Arg Lys Ser His Thr Glu Met Ser Lys Ser Ile Ser
                            565                 570                 575

Gln Leu Glu Ser Leu Asn Arg Glu Leu Gln Glu Arg Asn Arg Ile Leu
                        580                 585                 590

Glu Asn Ser Lys Ser Gln Thr Asp Lys Asp Tyr Tyr Gln Leu Gln Ala
                    595                 600                 605

Ile Leu Glu Ala Glu Arg Arg Asp Arg Gly His Asp Ser Glu Met Ile
            610                 615                 620

Gly Asp Leu Gln Ala Arg Ile Thr Ser Leu Gln Glu Glu Val Lys His
        625                 630                 635                 640

Leu Lys His Asn Leu Glu Lys Val Glu Gly Glu Arg Lys Glu Ala Gln
                            645                 650                 655

Asp Met Leu Asn His Ser Glu Lys Glu Lys Asn Asn Leu Glu Ile Asp
                        660                 665                 670

Leu Asn Tyr Lys Leu Lys Ser Leu Gln Gln Arg Leu Glu Gln Glu Val
                    675                 680                 685

Asn Glu His Lys Val Thr Lys Ala Arg Leu Thr Asp Lys His Gln Ser
                    690                 695                 700

Ile Glu Glu Ala Lys Ser Val Ala Met Cys Glu Met Glu Lys Lys Leu
        705                 710                 715                 720

Lys Glu Glu Arg Glu Ala Arg Glu Lys Ala Glu Asn Arg Val Val Gln
                            725                 730                 735

Ile Glu Lys Gln Cys Ser Met Leu Asp Val Asp Leu Lys Gln Ser Gln
                        740                 745                 750

Gln Lys Leu Glu His Leu Thr Gly Asn Lys Glu Arg Met Glu Asp Glu
                    755                 760                 765

Val Lys Asn Leu Thr Leu Gln Leu Glu Gln Glu Ser Asn Lys Arg Leu
            770                 775                 780

Leu Leu Gln Asn Glu Leu Lys Thr Gln Ala Phe Glu Ala Asp Asn Leu
        785                 790                 795                 800

Lys Gly Leu Glu Lys Gln Met Lys Gln Glu Ile Asn Thr Leu Leu Glu
                            805                 810                 815

Ala Lys Arg Leu Leu Glu Phe Glu Leu Ala Gln Leu Thr Lys Gln Tyr
                        820                 825                 830

Arg Gly Asn Glu Gly Gln Met Arg Glu Leu Gln Asp Gln Leu Glu Ala
                    835                 840                 845
```

```
Glu Gln Tyr Phe Ser Thr Leu Tyr Lys Thr Gln Val Lys Glu Leu Lys
850                 855                 860

Glu Glu Ile Glu Glu Lys Asn Arg Glu Asn Leu Lys Lys Ile Gln Glu
865                 870                 875                 880

Leu Gln Asn Glu Lys Glu Thr Leu Ala Thr Gln Leu Asp Leu Ala Glu
                    885                 890                 895

Thr Lys Ala Glu Ser Glu Gln Leu Ala Arg Gly Leu Leu Glu Glu Gln
            900                 905                 910

Tyr Phe Glu Leu Thr Gln Glu Ser Lys Lys Ala Ala Ser Arg Asn Arg
        915                 920                 925

Gln Glu Ile Thr Asp Lys Asp His Thr Val Ser Arg Leu Glu Glu Ala
930                 935                 940

Asn Ser Met Leu Thr Lys Asp Ile Glu Ile Leu Arg Arg Glu Asn Glu
945                 950                 955                 960

Glu Leu Thr Glu Lys Met Lys Lys Ala Glu Glu Tyr Lys Leu Glu
                965                 970                 975

Lys Glu Glu Glu Ile Ser Asn Leu Lys Ala Ala Phe Glu Lys Asn Ile
            980                 985                 990

Asn Thr Glu Arg Thr Leu Lys Thr Gln Ala Val Asn Lys Leu Ala Glu
        995                 1000                1005

Ile Met Asn Arg Lys Asp Phe Lys Ile Asp Arg Lys Lys Ala Asn
    1010                1015                1020

Thr Gln Asp Leu Arg Lys Lys Glu Lys Glu Asn Arg Lys Leu Gln
    1025                1030                1035

Leu Glu Leu Asn Gln Glu Arg Glu Lys Phe Asn Gln Met Val Val
    1040                1045                1050

Lys His Gln Lys Glu Leu Asn Asp Met Gln Ala Gln Leu Val Glu
    1055                1060                1065

Glu Cys Ala His Arg Asn Glu Leu Gln Met Gln Leu Ala Ser Lys
    1070                1075                1080

Glu Ser Asp Ile Glu Gln Leu Arg Ala Lys Leu Leu Asp Leu Ser
    1085                1090                1095

Asp Ser Thr Ser Val Ala Ser Phe Pro Ser Ala Asp Glu Thr Asp
    1100                1105                1110

Gly Asn Leu Pro Glu Ser Arg Ile Glu Gly Trp Leu Ser Val Pro
    1115                1120                1125

Asn Arg Gly Asn Ile Lys Arg Tyr Gly Trp Lys Lys Gln Tyr Val
    1130                1135                1140

Val Val Ser Ser Lys Lys Ile Leu Phe Tyr Asn Asp Glu Gln Asp
    1145                1150                1155

Lys Glu Gln Ser Asn Pro Ser Met Val Leu Asp Ile Asp Lys Leu
    1160                1165                1170

Phe His Val Arg Pro Val Thr Gln Gly Asp Val Tyr Arg Ala Glu
    1175                1180                1185

Thr Glu Glu Ile Pro Lys Ile Phe Gln Ile Leu Tyr Ala Asn Glu
    1190                1195                1200

Gly Glu Cys Arg Lys Asp Val Glu Met Glu Pro Val Gln Gln Ala
    1205                1210                1215

Glu Lys Thr Asn Phe Gln Asn His Lys Gly His Glu Phe Ile Pro
    1220                1225                1230

Thr Leu Tyr His Phe Pro Ala Asn Cys Asp Ala Cys Ala Lys Pro
    1235                1240                1245

Leu Trp His Val Phe Lys Pro Pro Pro Ala Leu Glu Cys Arg Arg
```

```
                1250                1255                1260
Cys His Val Lys Cys His Arg Asp His Leu Asp Lys Lys Glu Asp
        1265                1270                1275
Leu Ile Cys Pro Cys Lys Val Ser Tyr Asp Val Thr Ser Ala Arg
        1280                1285                1290
Asp Met Leu Leu Leu Ala Cys Ser Gln Asp Glu Gln Lys Lys Trp
        1295                1300                1305
Val Thr His Leu Val Lys Lys Ile Pro Lys Asn Pro Pro Ser Gly
        1310                1315                1320
Phe Val Arg Ala Ser Pro Arg Thr Leu Ser Thr Arg Ser Thr Ala
        1325                1330                1335
Asn Gln Ser Phe Arg Lys Val Val Lys Asn Thr Ser Gly Lys Thr
        1340                1345                1350
Ser

<210> SEQ ID NO 2
<211> LENGTH: 1388
<212> TYPE: PRT
<213> ORGANISM: Homo sapiens
<220> FEATURE:
<221> NAME/KEY: misc_feature
<223> OTHER INFORMATION: Rho-associated protein kinase 2 (ROCKII)

<400> SEQUENCE: 2

Met Ser Arg Pro Pro Thr Gly Lys Met Pro Gly Ala Pro Glu Thr
1                   5                   10                  15
Ala Pro Gly Asp Gly Ala Gly Ala Ser Arg Gln Arg Lys Leu Glu Ala
            20                  25                  30
Leu Ile Arg Asp Pro Arg Ser Pro Ile Asn Val Glu Ser Leu Leu Asp
        35                  40                  45
Gly Leu Asn Ser Leu Val Leu Asp Leu Asp Phe Pro Ala Leu Arg Lys
    50                  55                  60
Asn Lys Asn Ile Asp Asn Phe Leu Asn Arg Tyr Glu Lys Ile Val Lys
65                  70                  75                  80
Lys Ile Arg Gly Leu Gln Met Lys Ala Glu Asp Tyr Asp Val Val Lys
                85                  90                  95
Val Ile Gly Arg Gly Ala Phe Gly Glu Val Gln Leu Val Arg His Lys
            100                 105                 110
Ala Ser Gln Lys Val Tyr Ala Met Lys Leu Leu Ser Lys Phe Glu Met
        115                 120                 125
Ile Lys Arg Ser Asp Ser Ala Phe Phe Trp Glu Glu Arg Asp Ile Met
    130                 135                 140
Ala Phe Ala Asn Ser Pro Trp Val Val Gln Leu Phe Tyr Ala Phe Gln
145                 150                 155                 160
Asp Asp Arg Tyr Leu Tyr Met Val Met Glu Tyr Met Pro Gly Gly Asp
                165                 170                 175
Leu Val Asn Leu Met Ser Asn Tyr Asp Val Pro Glu Lys Trp Ala Lys
            180                 185                 190
Phe Tyr Thr Ala Glu Val Val Leu Ala Leu Asp Ala Ile His Ser Met
        195                 200                 205
Gly Leu Ile His Arg Asp Val Lys Pro Asp Asn Met Leu Leu Asp Lys
    210                 215                 220
His Gly His Leu Lys Leu Ala Asp Phe Gly Thr Cys Met Lys Met Asp
225                 230                 235                 240
Glu Thr Gly Met Val His Cys Asp Thr Ala Val Gly Thr Pro Asp Tyr
```

-continued

```
                245                 250                 255
Ile Ser Pro Glu Val Leu Lys Ser Gln Gly Asp Gly Phe Tyr Gly
            260                 265                 270
Arg Glu Cys Asp Trp Trp Ser Val Gly Val Phe Leu Tyr Glu Met Leu
            275                 280                 285
Val Gly Asp Thr Pro Phe Tyr Ala Asp Ser Leu Val Gly Thr Tyr Ser
        290                 295                 300
Lys Ile Met Asp His Lys Asn Ser Leu Cys Phe Pro Glu Asp Ala Glu
305                 310                 315                 320
Ile Ser Lys His Ala Lys Asn Leu Ile Cys Ala Phe Leu Thr Asp Arg
                325                 330                 335
Glu Val Arg Leu Gly Arg Asn Gly Val Glu Ile Arg Gln His Pro
            340                 345                 350
Phe Phe Lys Asn Asp Gln Trp His Trp Asp Asn Ile Arg Glu Thr Ala
            355                 360                 365
Ala Pro Val Val Pro Glu Leu Ser Ser Asp Ile Asp Ser Ser Asn Phe
        370                 375                 380
Asp Asp Ile Glu Asp Asp Lys Gly Asp Val Glu Thr Phe Pro Ile Pro
385                 390                 395                 400
Lys Ala Phe Val Gly Asn Gln Leu Pro Phe Ile Gly Phe Thr Tyr Tyr
                405                 410                 415
Arg Glu Asn Leu Leu Leu Ser Asp Ser Pro Ser Cys Arg Glu Thr Asp
            420                 425                 430
Ser Ile Gln Ser Arg Lys Asn Glu Glu Ser Gln Glu Ile Gln Lys Lys
            435                 440                 445
Leu Tyr Thr Leu Glu Glu His Leu Ser Asn Glu Met Gln Ala Lys Glu
        450                 455                 460
Glu Leu Glu Gln Lys Cys Lys Ser Val Asn Thr Arg Leu Glu Lys Thr
465                 470                 475                 480
Ala Lys Glu Leu Glu Glu Glu Ile Thr Leu Arg Lys Ser Val Glu Ser
                485                 490                 495
Ala Leu Arg Gln Leu Glu Arg Glu Lys Ala Leu Leu Gln His Lys Asn
            500                 505                 510
Ala Glu Tyr Gln Arg Lys Ala Asp His Glu Ala Asp Lys Lys Arg Asn
        515                 520                 525
Leu Glu Asn Asp Val Asn Ser Leu Lys Asp Gln Leu Glu Asp Leu Lys
        530                 535                 540
Lys Arg Asn Gln Asn Ser Gln Ile Ser Thr Glu Lys Val Asn Gln Leu
545                 550                 555                 560
Gln Arg Gln Leu Asp Glu Thr Asn Ala Leu Leu Arg Thr Glu Ser Asp
            565                 570                 575
Thr Ala Ala Arg Leu Arg Lys Thr Gln Ala Glu Ser Ser Lys Gln Ile
            580                 585                 590
Gln Gln Leu Glu Ser Asn Asn Arg Asp Leu Gln Asp Lys Asn Cys Leu
        595                 600                 605
Leu Glu Thr Ala Lys Leu Lys Leu Glu Lys Glu Phe Ile Asn Leu Gln
        610                 615                 620
Ser Ala Leu Glu Ser Glu Arg Arg Asp Arg Thr His Gly Ser Glu Ile
625                 630                 635                 640
Ile Asn Asp Leu Gln Gly Arg Ile Cys Gly Leu Glu Glu Asp Leu Lys
                645                 650                 655
Asn Gly Lys Ile Leu Leu Ala Lys Val Glu Leu Glu Lys Arg Gln Leu
            660                 665                 670
```

```
Gln Glu Arg Phe Thr Asp Leu Glu Lys Glu Lys Ser Asn Met Glu Ile
        675                 680                 685

Asp Met Thr Tyr Gln Leu Lys Val Ile Gln Gln Ser Leu Glu Gln Glu
        690                 695                 700

Glu Ala Glu His Lys Ala Thr Lys Ala Arg Leu Ala Asp Lys Asn Lys
705                 710                 715                 720

Ile Tyr Glu Ser Ile Glu Ala Lys Ser Glu Ala Met Lys Glu Met
            725                 730                 735

Glu Lys Lys Leu Leu Glu Glu Arg Thr Leu Lys Gln Lys Val Glu Asn
                740                 745                 750

Leu Leu Leu Glu Ala Glu Lys Arg Cys Ser Leu Leu Asp Cys Asp Leu
            755                 760                 765

Lys Gln Ser Gln Gln Lys Ile Asn Glu Leu Leu Lys Gln Lys Asp Val
    770                 775                 780

Leu Asn Glu Asp Val Arg Asn Leu Thr Leu Lys Ile Glu Gln Glu Thr
785                 790                 795                 800

Gln Lys Arg Cys Leu Thr Gln Asn Asp Leu Lys Met Gln Thr Gln Gln
                805                 810                 815

Val Asn Thr Leu Lys Met Ser Glu Lys Gln Leu Lys Gln Glu Asn Asn
                820                 825                 830

His Leu Met Glu Met Lys Met Asn Leu Glu Lys Gln Asn Ala Glu Leu
        835                 840                 845

Arg Lys Glu Arg Gln Asp Ala Asp Gly Gln Met Lys Glu Leu Gln Asp
        850                 855                 860

Gln Leu Glu Ala Glu Gln Tyr Phe Ser Thr Leu Tyr Lys Thr Gln Val
865                 870                 875                 880

Arg Glu Leu Lys Glu Glu Cys Glu Glu Lys Thr Lys Leu Gly Lys Glu
                885                 890                 895

Leu Gln Gln Lys Lys Gln Glu Leu Gln Asp Glu Arg Asp Ser Leu Ala
                900                 905                 910

Ala Gln Leu Glu Ile Thr Leu Thr Lys Ala Asp Ser Glu Gln Leu Ala
        915                 920                 925

Arg Ser Ile Ala Glu Glu Gln Tyr Ser Asp Leu Glu Lys Glu Lys Ile
    930                 935                 940

Met Lys Glu Leu Glu Ile Lys Glu Met Met Ala Arg His Lys Gln Glu
945                 950                 955                 960

Leu Thr Glu Lys Asp Ala Thr Ile Ala Ser Leu Glu Glu Thr Asn Arg
            965                 970                 975

Thr Leu Thr Ser Asp Val Ala Asn Leu Ala Asn Glu Lys Glu Glu Leu
            980                 985                 990

Asn Asn Lys Leu Lys Asp Val Gln Glu Gln Leu Ser Arg Leu Lys Asp
        995                 1000                1005

Glu Glu Ile Ser Ala Ala Ala Ile Lys Ala Gln Phe Glu Lys Gln
    1010                1015                1020

Leu Leu Thr Glu Arg Thr Leu Lys Thr Gln Ala Val Asn Lys Leu
    1025                1030                1035

Ala Glu Ile Met Asn Arg Lys Glu Pro Val Lys Arg Gly Asn Asp
    1040                1045                1050

Thr Asp Val Arg Arg Lys Glu Lys Glu Asn Arg Lys Leu His Met
    1055                1060                1065

Glu Leu Lys Ser Glu Arg Glu Lys Leu Thr Gln Gln Met Ile Lys
    1070                1075                1080
```

Tyr Gln Lys Glu Leu Asn Glu Met Gln Ala Gln Ile Ala Glu Glu
1085                1090                1095

Ser Gln Ile Arg Ile Glu Leu Gln Met Thr Leu Asp Ser Lys Asp
1100                1105                1110

Ser Asp Ile Glu Gln Leu Arg Ser Gln Leu Gln Ala Leu His Ile
1115                1120                1125

Gly Leu Asp Ser Ser Ile Gly Ser Gly Pro Gly Asp Ala Glu
1130                1135                1140

Ala Asp Asp Gly Phe Pro Glu Ser Arg Leu Glu Gly Trp Leu Ser
1145                1150                1155

Leu Pro Val Arg Asn Asn Thr Lys Lys Phe Gly Trp Val Lys Lys
1160                1165                1170

Tyr Val Ile Val Ser Ser Lys Lys Ile Leu Phe Tyr Asp Ser Glu
1175                1180                1185

Gln Asp Lys Glu Gln Ser Asn Pro Tyr Met Val Leu Asp Ile Asp
1190                1195                1200

Lys Leu Phe His Val Arg Pro Val Thr Gln Thr Asp Val Tyr Arg
1205                1210                1215

Ala Asp Ala Lys Glu Ile Pro Arg Ile Phe Gln Ile Leu Tyr Ala
1220                1225                1230

Asn Glu Gly Glu Ser Lys Lys Glu Gln Glu Phe Pro Val Glu Pro
1235                1240                1245

Val Gly Glu Lys Ser Asn Tyr Ile Cys His Lys Gly His Glu Phe
1250                1255                1260

Ile Pro Thr Leu Tyr His Phe Pro Thr Asn Cys Glu Ala Cys Met
1265                1270                1275

Lys Pro Leu Trp His Met Phe Lys Pro Pro Ala Leu Glu Cys
1280                1285                1290

Arg Arg Cys His Ile Lys Cys His Lys Asp His Met Asp Lys Lys
1295                1300                1305

Glu Glu Ile Ile Ala Pro Cys Lys Val Tyr Tyr Asp Ile Ser Thr
1310                1315                1320

Ala Lys Asn Leu Leu Leu Leu Ala Asn Ser Thr Glu Glu Gln Gln
1325                1330                1335

Lys Trp Val Ser Arg Leu Val Lys Lys Ile Pro Lys Lys Pro Pro
1340                1345                1350

Ala Pro Asp Pro Phe Ala Arg Ser Ser Pro Arg Thr Ser Met Lys
1355                1360                1365

Ile Gln Gln Asn Gln Ser Ile Arg Arg Pro Ser Arg Gln Leu Ala
1370                1375                1380

Pro Asn Lys Pro Ser
1385

<210> SEQ ID NO 3
<211> LENGTH: 15
<212> TYPE: PRT
<213> ORGANISM: Artificial Sequence
<220> FEATURE:
<223> OTHER INFORMATION: Synthesized Sequence

<400> SEQUENCE: 3

```
Arg Ala Ser Pro Arg Ala Ser Pro Arg Thr Leu Ser Thr Arg Ser
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Synthesized Sequence,
<220> FEATURE:
<221> NAME/KEY: misc_feature
<222> LOCATION: (8)..(8)
<223> OTHER INFORMATION: Ser is phosphated

<400> SEQUENCE: 4

Arg Ala Ser Pro Arg Thr Leu Ser Thr Arg Ser
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthesized Sequence

<400> SEQUENCE: 5

Asp Pro Phe Ala Arg Ser Ser Pro Arg Thr Ser Met Lys
1               5                   10

<210> SEQ ID NO 6
<211> LENGTH: 13
<212> TYPE: PRT
<213> ORGANISM: Artificial Sequence
<220> FEATURE:
<223> OTHER INFORMATION: Synthesized Sequence
<220> FEATURE:
<221> NAME/KEY: misc_feature
<222> LOCATION: (11)..(11)
<223> OTHER INFORMATION: Ser is phosphated

<400> SEQUENCE: 6

Asp Pro Phe Ala Arg Ser Ser Pro Arg Thr Ser Met Lys
1               5                   10
```